(12) United States Patent
Joji (10) Patent No.: US 11,073,526 B2
(45) Date of Patent: Jul. 27, 2021

(54) AUTOMATIC ANALYSIS DEVICE (71) Applicant: HITACHI HIGH-TECHNOLOGIES CORPORATION, Tokyo (JP)

(72) Inventor: Akira Joji, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 265 days.

(21) Appl. No.: 16/072,956

(22) PCT Filed: Jan. 12, 2017

(86) PCT No.: PCT/JP2017/000702
§ 371 (c)(1),
(2) Date: Jul. 26, 2018

(87) PCT Pub. No.: WO2017/138285
PCT Pub. Date: Aug. 17, 2017

(65) Prior Publication Data
US 2019/0033332 A1  Jan. 31, 2019

(30) Foreign Application Priority Data

Feb. 10, 2016 (JP) .............................. JP2016-023232

(51) Int. Cl.
*G01N 35/02* (2006.01)
*G01N 35/04* (2006.01)
(Continued)

(52) U.S. Cl.
CPC ....... *G01N 35/025* (2013.01); *G01N 35/0092* (2013.01); *G01N 35/04* (2013.01);
(Continued)

(58) Field of Classification Search
CPC .............. G01N 21/00; G01N 33/4905; G01N 35/00584; G01N 35/00722;
(Continued)

(56) References Cited

U.S. PATENT DOCUMENTS

| 5,677,188 A | 10/1997 | Mitsumaki et al. |
| 2012/0048036 A1 | 3/2012 | Mimura et al. |

(Continued)

FOREIGN PATENT DOCUMENTS

| EP | 1 672 370 A1 | 6/2006 | |
| EP | 1672370 A1 * | 6/2006 | ......... G01N 35/0092 |

(Continued)

OTHER PUBLICATIONS

International Search Report of PCT/JP2017/000702 dated May 23, 2017.

(Continued)

*Primary Examiner* — Matthew D Krcha
*Assistant Examiner* — Austin Q Le
(74) *Attorney, Agent, or Firm* — Mattingly & Malur, PC (57) ABSTRACT

In blood clotting tests, a reagent is mixed with a sample and a blood clotting reaction is initiated. The time from initiation until the reaction is complete is not fixed. As a result, during analysis, whether or not the blood clotting reaction is complete is judged at fixed intervals based on the measured amount of scattered light. Therefore, time is wasted and analysis cannot be conducted efficiently if the blood clotting reaction reaches completion more quickly than predicted. Accordingly, the automatic analysis device and method takes this problem into consideration. When information about a plurality of samples is entered, the device compares the predicted reaction time length of each requested analysis item for the plurality of samples, determines an analysis sequence to carry out the analysis for each item in order from longest to shortest, and carries out the analysis on the basis of the determined analysis sequence.

5 Claims, 7 Drawing Sheets

(51) Int. Cl.
*G01N 35/10* (2006.01)
*G01N 35/00* (2006.01)
*G01N 33/49* (2006.01)

(52) U.S. Cl.
CPC ......... *G01N 35/10* (2013.01); *G01N 33/4905* (2013.01); *G01N 2035/0097* (2013.01); *G01N 2035/00564* (2013.01); *G01N 2035/0441* (2013.01); *G01N 2035/0443* (2013.01); *G01N 2035/1076* (2013.01); *G01N 2035/1086* (2013.01)

(58) Field of Classification Search
CPC ......... G01N 35/00732; G01N 35/0092; G01N 35/02; G01N 35/025; G01N 35/026; G01N 35/04; G01N 35/0401; G01N 35/10; G01N 2035/00564; G01N 2035/00841; G01N 2035/00851; G01N 2035/0097; G01N 2035/0401; G01N 2035/0439; G01N 2035/0441; G01N 2035/0443; G01N 2035/0444; G01N 2035/1002; G01N 2035/1076; G01N 2035/1086; G01N 2035/1088; G01N 33/83
See application file for complete search history.

(56) References Cited

U.S. PATENT DOCUMENTS

| | | | | |
|---|---|---|---|---|
| 2013/0046480 A1* | 2/2013 | Manri | ............. | G01N 35/00584 702/19 |
| 2014/0348704 A1* | 11/2014 | Kobayashi | ......... | G01N 35/0092 422/67 |

FOREIGN PATENT DOCUMENTS

| | | | | |
|---|---|---|---|---|
| JP | 05-002024 A | | 1/1993 | |
| JP | 09-257804 A | | 10/1997 | |
| JP | 2001-174468 A | | 6/2001 | |
| JP | 2010-181197 A | | 8/2010 | |
| JP | 2010181197 A | * | 8/2010 | ....... G01N 35/00732 |
| JP | 2011-153943 A | | 8/2011 | |
| WO | 2010/090138 A1 | | 8/2010 | |
| WO | 2010/117045 A1 | | 10/2010 | |

OTHER PUBLICATIONS

International Preliminary Report on Patentability received in corresponding International Application No. PCT/JP2017/000702 dated Aug. 16, 2018.
Extended European Search Report received in corresponding European Application No. 17750010.5 dated Sep. 23, 2019.

* cited by examiner

EXAMPLE OF ANALYSIS ITEMS — 301

(A) CONVENTIONAL EXAMPLE (1)

| No. | SAMPLE | ANALYSIS ITEM | REACTION TIME |
|---|---|---|---|
| 1 | A | aaa | 5 |
| 2 | A | bbb | 4 |
| 3 | A | ccc | 3 |
| 4 | B | bbb | 4 |
| 5 | B | ccc | 3 |
| 6 | B | ddd | 2 |
| 7 | C | ccc | 3 |
| 8 | C | ddd | 2 |
| 9 | C | eee | 1 |
| 10 | C | aaa | 5 |

(B) CONVENTIONAL EXAMPLE (2)

| No. | SAMPLE | ANALYSIS ITEM | REACTION TIME |
|---|---|---|---|
| 1 | A | aaa | 5 |
| 2 | A | bbb | 4 |
| 3 | A | ccc | 3 |
| 4 | B | bbb | 4 |
| 5 | B | ccc | 3 |
| 6 | B | ddd | 2 |
| 7 | C | aaa | 5 |
| 8 | C | ccc | 3 |
| 9 | C | ddd | 2 |
| 10 | C | eee | 1 |

(C) EMBODIMENT

| No. | SAMPLE | ANALYSIS ITEM | REACTION TIME |
|---|---|---|---|
| 1 | A | aaa | 5 |
| 2 | C | aaa | 5 |
| 3 | A | bbb | 4 |
| 4 | B | bbb | 4 |
| 5 | A | ccc | 3 |
| 6 | B | ccc | 3 |
| 7 | C | ccc | 3 |
| 8 | B | ddd | 2 |
| 9 | C | ddd | 2 |
| 10 | C | eee | 1 |

* CONVENTIONAL EXAMPLE (1): IN ORDER OF REQUEST RECEIPT
  CONVENTIONAL EXAMPLE (2): DETERMINE MEASUREMENT ORDER FOR EACH SAMPLE

302

| SAMPLE A IN ANALYSIS | |
| SAMPLE B IN ANALYSIS | |
| SAMPLE C IN ANALYSIS | |
| IN PREPARATION OPERATION | |

EXAMPLE OF ANALYSIS ITEMS (A) CONVENTIONAL EXAMPLE (1)

| No. | SAMPLE | ANALYSIS ITEM | REACTION TIME |
|---|---|---|---|
| 1 | A | aaa | 5 |
| 2 | A | bbb | 4 |
| 3 | A | ccc | 3 |
| 4 | B | bbb | 4 |
| 5 | B | ccc | 3 |
| 6 | B | ddd | 2 |
| 7 | C | ccc | 3 |
| 8 | C | ddd | 2 |
| 9 | C | eee | 1 |
| 10 | C | aaa | 5 |

(B) CONVENTIONAL EXAMPLE (2)

| No. | SAMPLE | ANALYSIS ITEM | REACTION TIME |
|---|---|---|---|
| 1 | A | aaa | 5 |
| 2 | A | bbb | 4 |
| 3 | A | ccc | 3 |
| 4 | B | bbb | 4 |
| 5 | B | ccc | 3 |
| 6 | B | ddd | 2 |
| 7 | C | aaa | 5 |
| 8 | C | ccc | 3 |
| 9 | C | ddd | 2 |
| 10 | C | eee | 1 |

(C) EMBODIMENT — 501

| No. | SAMPLE | ANALYSIS ITEM | REACTION TIME |
|---|---|---|---|
| 1 | A | aaa | 5 |
| 2 | C | aaa | 5 |
| 3 | A | bbb | 4 |
| 4 | B | bbb | 4 |
| 5 | A | ccc | 3 |
| 6 | C | eee | 1 |
| 7 | B | ccc | 3 |
| 8 | C | ccc | 3 |
| 9 | B | ddd | 2 |
| 10 | C | ddd | 2 |

\* CONVENTIONAL EXAMPLE (1): IN ORDER OF REQUEST RECEIPT
CONVENTIONAL EXAMPLE (2): DETERMINE MEASUREMENT ORDER FOR EACH SAMPLE

502

| SAMPLE A IN ANALYSIS | |
| SAMPLE B IN ANALYSIS | |
| SAMPLE C IN ANALYSIS | |
| IN PREPARATION OPERATION | |

[Fig. 5] CONTINUED

AUTOMATIC ANALYSIS DEVICE

TECHNICAL FIELD

The present invention relates to an automatic analysis device for automatically analyzing components of blood or the like.

BACKGROUND ART

As a device for analyzing a target component contained in a biological sample such as blood, an automatic analysis device that measures an amount of transmitted light or scattered light of a single or plural wavelengths obtained by irradiating a reaction solution which is a mixture of a sample and a reagent with light from a light source has been widely used.

Here, examples of such automatic analysis devices include a biochemical analysis device that quantitatively or qualitatively analyzes a target component in a biological sample and a blood clotting analysis device that measures coagulability of a sample blood, in the field of biochemical test, hematology test, and the like.

In the case of test items for the former biochemical analysis, reaction times are predetermined and thus measurements can be scheduled according to the reaction times. However, in the case of test items for the latter blood clotting analysis, the reaction times are not fixed and therefore whether or not the blood clotting reaction is complete has to be judged at fixed intervals based on the measured amount of light. Accordingly, the actual measurement time to complete the reaction is sometimes shorter than the predicted reaction time depending on the state of the reagent or sample or the measurement conditions. Since the reaction completion time thus irregularly varies in blood clotting analyses, wasted time sometimes occurs in the time period required until the analyses of all the requested test items are complete, preventing the efficient analysis.

For the purpose of reducing the analysis processing time of a sample for which plural items are analyzed, PTL 1 describes a technique in which when an instruction to measure plural analysis items is given for one sample, the items are allocated to reaction vessels sequentially from the item that requires the longest processing time.

CITATION LIST

Patent Literature

PTL 1: JP-A-5-2024

SUMMARY OF INVENTION

Technical Problem

In recent years, it has been required in automatic analysis devices that the entire analysis is efficiently and rapidly processed. In particular, since the importance of blood clotting analyses is being enhanced, such a demand is being increased. According to the technique disclosed in PTL 1, however, the time until the measurement results of plural test items in a single sample unit are output can be reduced, but optimization of all the test items for the plural samples requested is never considered. The technique also does not meet the case where the reaction time varies depending on the state or conditions and where the number of reaction ports (areas which each includes a reaction vessel placement unit, a light source, and a detection unit and where optical measurements are performed) is limited to less than in biochemical analyses as in the aforementioned blood clotting analysis. Accordingly, particularly in a blood clotting analysis, wasted time remains to occur in the whole analysis in some cases.

Solution to Problem

An aspect for solving the above problem, provided is a device including: a sample vessel for holding a sample; a reagent vessel for holding a reagent; a sample dispensing mechanism for dispensing the sample from the sample vessel; a reagent dispensing mechanism for dispensing the reagent from the reagent vessel; a reaction vessel for holding a mixed solution of the sample dispensed from the sample dispensing mechanism and the reagent dispensed from the reagent dispensing mechanism; an analysis unit that includes a plurality of reaction vessel placement units for placement of the reaction vessel therein, each of the plurality of reaction vessel placement units being provided with a light source for emitting light to the reaction vessel holding the mixed solution and a light receiving unit for receiving the light emitted from the light source; an operating unit for input of information about the sample therein; a control unit for controlling the analysis unit based on the input information, wherein the control unit when information about a plurality of samples is input from the operating unit, compares predicted reaction time lengths of analysis items requested for the plurality of samples, while determining an analysis order so that analyses of the analysis items are performed in descending order of the predicted reaction time length, calculates a proportion of analysis items for which the predicted reaction time satisfies a predetermined condition to all the analysis items based on the result of the comparison of the predicted reaction time lengths of the analysis items requested for the plurality of samples, calculates the number of the reaction vessel placement units where the analysis items for which the predicted reaction time satisfies the predetermined condition are preferentially analyzed among the plurality of reaction vessel placement units in the analysis unit based on the calculated proportion, and while controlling the analysis unit based on the determined analysis order, controls the analysis unit to preferentially analyze the analysis items for which the predicted reaction time satisfies the predetermined condition in the calculated number of the reaction vessel placement units. A method using the device is also provided.

Advantageous Effects of Invention

The aforementioned aspect enables reduction of the time required until analyses of all test items requested for a plurality of specimens are complete, thereby realizing a more efficient and rapid analysis.

DESCRIPTION OF EMBODIMENTS

Embodiments of the present invention will be described in detail below with reference to drawings. Components having the same function across figures are given the same sign throughout the description in principle and the explanation is omitted in some cases.
(Overall Configuration of Device)

Figure 1:
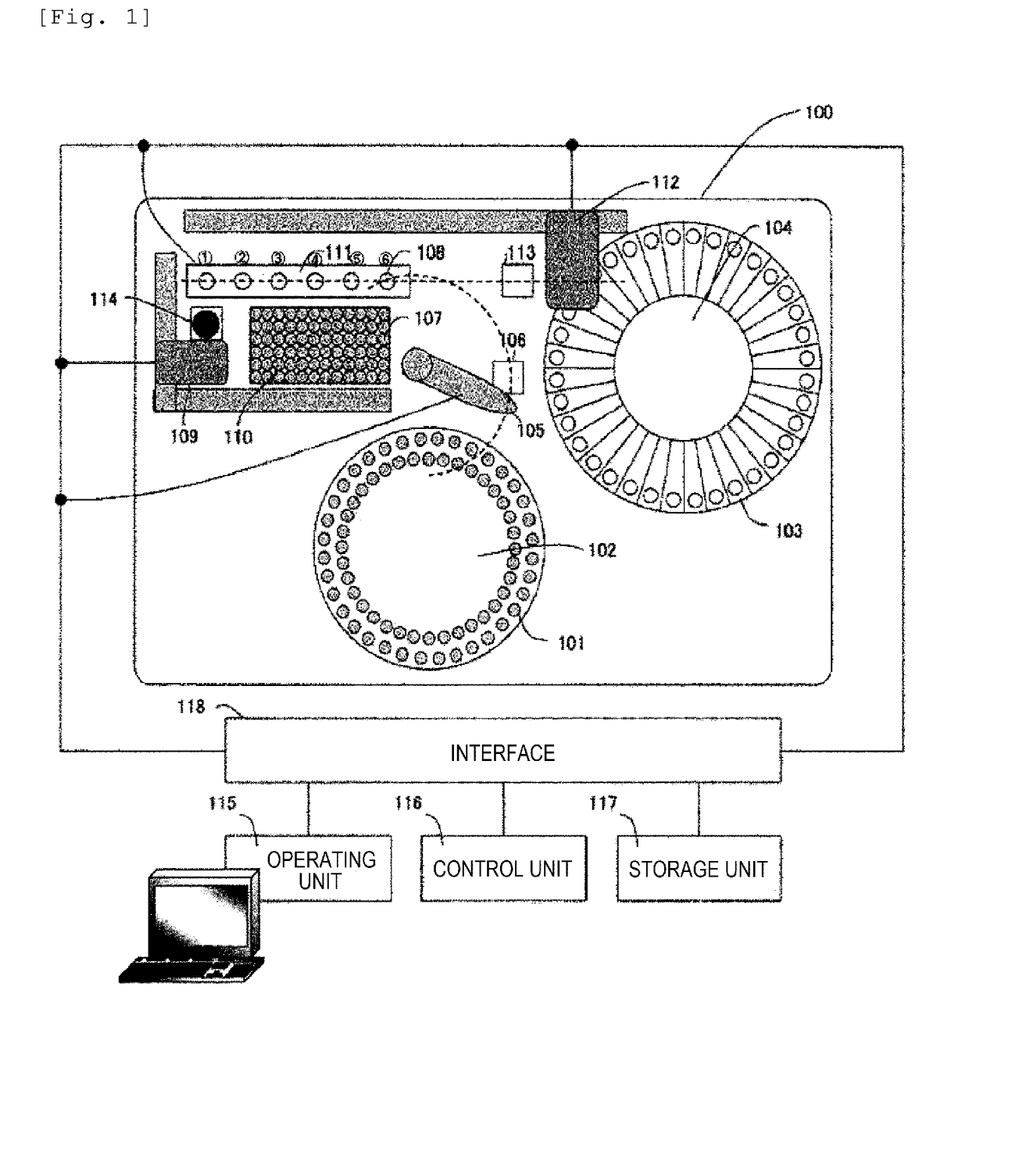
FIG. 1 is a diagram showing a basic configuration of the automatic analysis device according to the embodiment.

FIG. 1 shows a basic configuration of the automatic analysis device according to the embodiment. Here, as one aspect of the automatic analysis device, an example of a device performing a blood clotting analysis will be described.

As shown in FIG. 1, an automatic analysis device 100 is mainly composed of sample vessels 101, a sample disk 102, reagent vessels 103, a reagent disk 104, a sample dispensing mechanism 105, a sample dispensing position 106, reaction vessels 107, reaction vessel placement units 108, a reaction vessel transporting mechanism 109, a reaction vessel stock unit 110, reaction ports 111, a reagent dispensing mechanism 112, a reagent dispensing mechanism washing mechanism 113, a reaction vessel disposing unit 114, an operating unit 115, a control unit 116, a storage unit 117, and an interface 118.

The sample vessel 101 holds a sample or an accuracy control sample. The sample disk 102 holds a plurality of the sample vessels 101, and rotates in a clockwise or counterclockwise direction to transport a target one of the sample vessels 101 to a position where the sample dispensing mechanism 105 sucks the sample in the sample vessel 101. The reagent vessel 103 holds a reagent. The reagent disk 104 holds a plurality of the reagent vessels 103, and rotates in a clockwise or counterclockwise direction to transport a target one of the reagent vessels 103 to a position where the reagent dispensing mechanism 112 sucks the reagent in the reagent vessel 103.

The sample dispensing mechanism 105 sucks the sample in the sample vessel 101 held in the sample disk 102 by an operation of a sample syringe (not shown) controlled by the control unit 116 and discharges the sample into the reaction vessel 107. The sample dispensing position 106 is a place for storing the sample in the reaction vessel 107. The reaction vessel 107 is transported to the sample dispensing position 106 by the reaction vessel transporting mechanism 109. After the transportation of the reaction vessel 107, the sample is discharged from the sample vessel 101 by the sample dispensing mechanism 105. After the discharge of the sample, the reaction vessel 107 holding the sample is transported to the reaction vessel placement unit 108 by the reaction vessel transporting mechanism 109.

The reaction vessel 107 is a container for holding a mixed solution of the sample and the reagent dispensed. The reaction vessel transporting mechanism 109 transports the reaction vessel 107 that is empty held in the reaction vessel stock unit 110 to the reaction vessel placement unit 108, and transports the reaction vessel 107 whose analysis is complete from the reaction vessel placement unit 108 to the reaction vessel disposing unit 114. The reaction vessel stock unit 110 holds a plurality of the reaction vessels 107 that are unused.

The reaction port 111 includes one or more (6 in the embodiment as one example) reaction vessel placement units 108 for placement of the reaction vessel 107 therein, and measures an optical intensity from a reaction solution contained in the reaction vessel 107 inserted in each of the reaction vessel placement units 108. For this purpose, each of the reaction vessel placement units 108 includes one light source (not shown) for emitting incident light to the reaction solution and one detection unit (optical sensor) for measuring the optical intensity inside the placement unit. The light source is placed on the bottom surface of the reaction vessel placement unit 108 and can emit light upward. The light scattered by the reaction solution is detected. The detection unit is placed on the side surface of the reaction vessel placement unit 108, and subjects the detected light to light/current conversion and outputs an optical measurement signal indicative of the optical intensity to an A/D converter. A measurement signal of the optical intensity A/D-converted in the A/D converter is sent via the interface 118 to the control unit 116 and to the storage unit 117. The arrangement of the light source and the detector is not necessarily limited to the above positional relation, and other arrangement may be adopted as long as the optical intensity from the reaction solution can be detected.

The reagent dispensing mechanism 112 dispenses a reagent in the reagent vessel 103 held in the reagent disk 104 into the reaction vessel 107 placed in the reaction port 111 by an operation of a reagent syringe (not shown) controlled by the control unit 116. A reagent heating mechanism (not shown) controlled by the control unit 116 is built in the reagent dispensing mechanism 112 and heating a sucked reagent to an appropriate temperature (a prescribed temperature). The reagent dispensing mechanism washing mechanism 113 is a mechanism for washing the reagent dispensing mechanism 112 with water. The timing of the water washing is controlled by the control unit 116.

The reaction vessel disposing unit 114 disposes the reaction vessel 107.

The operating unit 115 is a computer that has an input terminal, such as a keyboard, a mouse, and an operation screen displayed on a display unit, as an input measure. Test items of samples to be analyzed are input from the keyboard or the operation screen provided in the operating unit 115 and then are input into the control unit 116. The control unit 116 controls the operations of the sample disk 102, the reagent disk 104, the sample dispensing mechanism 105, the reaction vessel transferring mechanism 109, the reaction port 111, the reagent dispensing mechanism 112, and the reagent dispensing mechanism washing mechanism. 113 based on the input from the operating unit 115. The control unit 116 processes a measurement signal input from the detection unit 111 via the interface 118 to calculate a blood clotting time or specify an abnormal part. The detail will be described later. The storage unit 117 stores, for example, input information from the operating unit 115, operation information of the sample disk 102 and the like, and information about reagents and samples. The interface 118 mediates between operation information of the sample disk 102 and the like and input information from the operating unit 115, and between operation information from the control unit 116 and information stored in the storage unit 117.

The control unit 116 in FIG. 1 is connected to each constituent unit via the interface 118 to control the entire automatic analysis device, but an independent control unit may be provided for each constituent unit.

Here, a basic analysis operation in the automatic analysis device 100 will be described. An analysis of a sample is basically performed in the order of sample dispensing, reagent dispensing, optical measurement, disposing of the reaction vessel 107, and a data processing. A plurality of the reaction vessels 107 are arranged lengthwise and crosswise on the reaction vessel stock unit 110. The reaction vessel transporting mechanism 109 transports the reaction vessels 107 in the prescribed order from the reaction vessel stock unit 110 to the reaction vessel placement unit 108. On the sample disk 102, a plurality of the sample vessels 101 are arranged in a row on the circumference, and the sample disk 102 rotates in the clockwise or counterclockwise direction according to the order of the samples to be analyzed to transport the sample vessels 101 to a position under the sample dispensing mechanism 105. The sample in the sample vessel 101 is sucked in a prescribed amount by the sample syringe (not shown) connected to the sample dispensing mechanism 105 and is dispensed into the reaction vessel 107.

On the reagent disk 104, a plurality of the reagent vessels 103 are arranged in a row on the circumference, and when receiving instructions to select a test item and to start the analysis from the operating unit 115, the reagent disk 104 rotates in the clockwise or counterclockwise direction to transport the target reagent vessel 103 according to the test item to a position under the reagent dispensing mechanism 112. The reagent in the reagent vessel 103 is sucked in a prescribed amount by the reagent syringe (not shown) connected to the reagent dispensing mechanism 112 and is dispensed into the reaction vessel 107.

Next, in the reaction vessel 107 holding the content (mixed solution), a blood clotting reaction proceeds through mixing of the sample with the reagent. When the mixed solution receives a luminous flux from the light source (not shown), the luminous flux is scattered by a solid produced by the blood clotting reaction in the mixed solution. At this time, the optical intensity scattered by the mixed solution is detected by the detection unit and is sensed by the reaction port 111. Analysis information, such as the sensed optical intensity which is measurement data, the reaction port number used, the type of sample used, the placement position on the sample disk 102, the type of reagent used, and the placement position on the reagent disk 104, is stored in the storage unit 117.

The control unit 116 determines at fixed intervals whether or not the blood clotting reaction is complete by using the sensed measurement data. When the reaction is complete, the blood clotting time is calculated by the control unit 116, and the result file is stored in the storage unit 117 and is output to an output device, such as a display, included in the operating unit 115. When the reaction is not complete, the measurement is stopped at the time when the measurement time set by the operating unit 115 is reached. Subsequently, the blood clotting time is calculated by the control unit 116, and the result file is stored in the storage unit 117 and is output to an output device, such as a display, included in the operating unit 115.

First Embodiment

Figure 2:
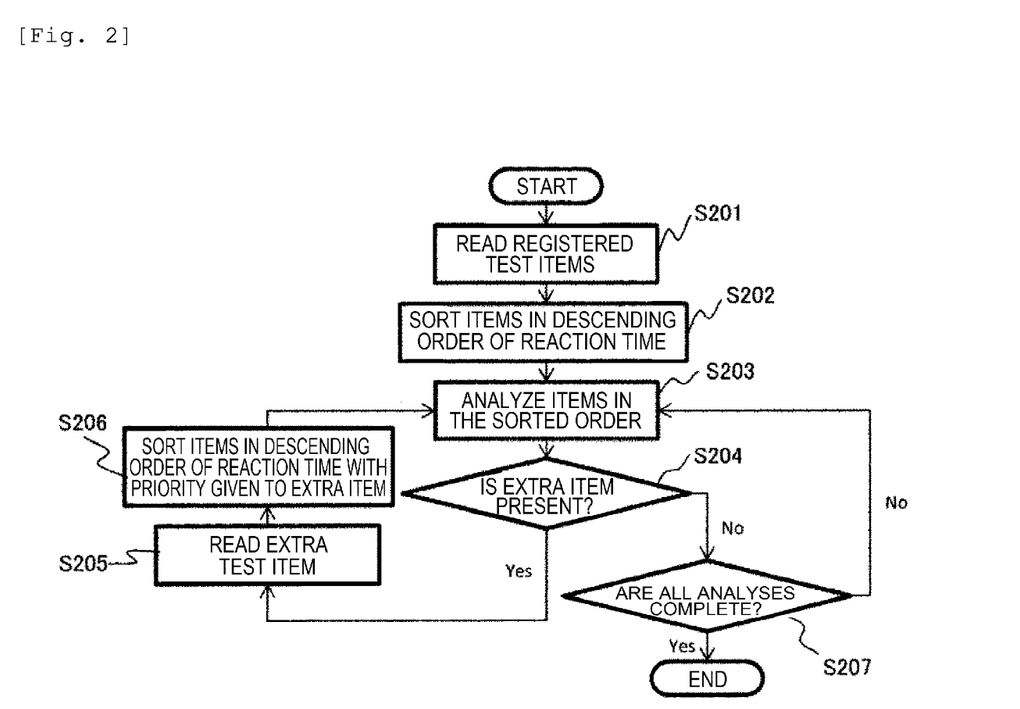
FIG. 2 is a flow chart for explaining an operation control for determining a measurement order of test items in the automatic analysis device according to the embodiment (a first embodiment).

Next, the embodiment will be explained based on FIG. 2. FIG. 2 is a flow chart for explaining an operation control for determining the measurement order of test items according to the embodiment.

The flow chart shown in FIG. 2 shows a flow of a processing in the automatic analysis device 100, in which a user inputs analysis parameters required for registration of test items into the automatic analysis device 100 via the operating unit 115 in advance, sets a sample and a reagent, and then starts analysis operations, and finally completion of the sample analyses is reached.

When receiving the instruction to start the analysis from the user, the automatic analysis device 100 reads out information (analysis items) imparted to each sample (step S201). An example using a bar cord is described here. Information of items to be analyzed for a sample is contained in a bar cord attached to the sample and is read out by a bar cord reader (not shown). The control unit 116 sends the information (test items) read out by the bar cord reader to the operating unit 115. The operating unit 115 compares the test item information sent from the control unit 116 to information registered by the user, and sends information of the coincident test items (information required for performing the analysis operations, such as analysis parameters) to the control unit 116. The control unit 116 can thus read out analysis parameters of analysis items of samples to be tested.

Next, the predicted measurement times (hereinafter, sometimes simply referred to as predicted times) which are one of the analysis parameters read for each test item are read out and the test items are sorted in descending order of the predicted time length (step S202). The automatic analysis device 100 dispenses samples and reagents in the order sorted in step S202 and performs the analyses (step S203). Here, the analyses are performed along the operations by the constituents of the automatic analysis device 100 described in FIG. 1.

Here, when a reaction of a sample being analyzed is complete in a shorter time than the predicted measurement time, each mechanism operates so as to use the reaction port for an analysis of the next sample without waiting until the predicted time is reached. Such an operation of each mechanism means, for example, that even when all the reaction ports 111 are used for analyses, the sample to be analyzed next is dispensed by the reagent dispensing mechanism 112 at the sample dispensing position 106 into an unused one of the reaction vessels 107 and is allowed to wait. Accordingly, as soon as the analysis of the sample in the reaction port 111 is complete, the reaction vessel 107 holding a sample for which the analysis is complete can be disposed to start transportation of the reaction vessel 107 for the next analysis to the reaction port 111 and analysis thereof. Thus, the reaction ports 111 can be efficiently used to perform continuous analyses.

Monitoring whether or not there is a request of an extra analysis, for example, an analysis of an urgent specimen which has to be analyzed as a top priority is performed in the analyses (step S204). Here, the monitoring refers to regular communication of the automatic analysis device 100 with the operating unit 115. When an analysis of an urgent specimen is requested, the operating unit 115 sends the content of the analysis request to the automatic analysis device 110 in the regular communication.

When an extra analysis arises, the test item of the extra analysis is read out (step S205). Next, in step S206, the test item read in step S205 is combined with the test items which are read in step S201 and are sorted in step S202, and the combined test items are re-sorted in descending order of the measurement time length (step S206). Then, the process returns to step S203, and starts the analyses in the order re-sorted in step S206. When no extra analysis arises, whether or not the analyses of all the requested test items are complete is determined every time a measurement of a test item is complete (step S207). When all the requested items are not complete, the process returns to step S203, and the remaining items are analyzed in the sorted order. When it is determined that the analyses of all the requested items are complete in step S207, the analysis operation is ended.

The effect of the embodiment will be described. As described above, the measurement time sometimes varies relative to a measurement time predicted before the start of an analysis operation depending on the state of the samples and reagents as in a blood clotting analysis. In addition, in an analysis condition where the number of the reaction ports is limited, when an analysis plan made prior to the start of the analysis operation is performed by a conventional technique, wasted time occurs until a plurality of test items for all samples requested are complete, and the analysis efficiency may thus be lowered.

If wasted time occurs until the analyses of the test items are complete, wasted time also occurs in the time until the test operator receives the test results (turnaround time), affecting the final diagnosis time. Since there may be a highly urgent test item particularly in a blood clotting test, the wasted time in turnaround time is a very important problem.

In contrast, according to the embodiment, all test items requested before analysis operation are re-sorted in descending order of the measurement time length regardless of the difference in sample types. This enables sequential analyses from an item that requires a longer measurement time, and thus all requested analysis items of all specimens can be analyzed in the most efficient manner. Even if a blood clotting reaction of one sample is complete in a shorter time than the measurement time, occurrence of wasted time is prevented by analyzing next the test item requiring the longest measurement time among the remaining test items, and thus the analyses can be efficiently continued.

Furthermore, in the automatic analysis device according to the embodiment, when a blood clotting reaction of a sample being analyzed is complete in a shorter time than the predicted reaction time, each mechanism operates so as to use the reaction port for the analysis of the next sample without waiting until the predicted time is elapsed. This results in reduction of time loss with no analysis operation, the blood clotting analyses can be continuously performed, and the reaction vessels can be efficiently used, as compared with a configuration where operations for dispensing, measurement, and the like have to be performed at predetermined timings for a certain period of time even when any analysis is cancelled as in the case of a biochemical analysis automatic analysis device. As described above, when all test items of all samples are analyzed in descending order of the measurement time length beyond the difference in sample types, the analyses of all the test items can be complete in a shorter time than in the case where the test items are re-sorted in descending order of the measurement time length for each sample. Accordingly, it is possible to increase the efficiency of the whole procedure until the tests of all requested test items are complete, and to rapidly provide the test results of the test items to a user.

Figure 3:
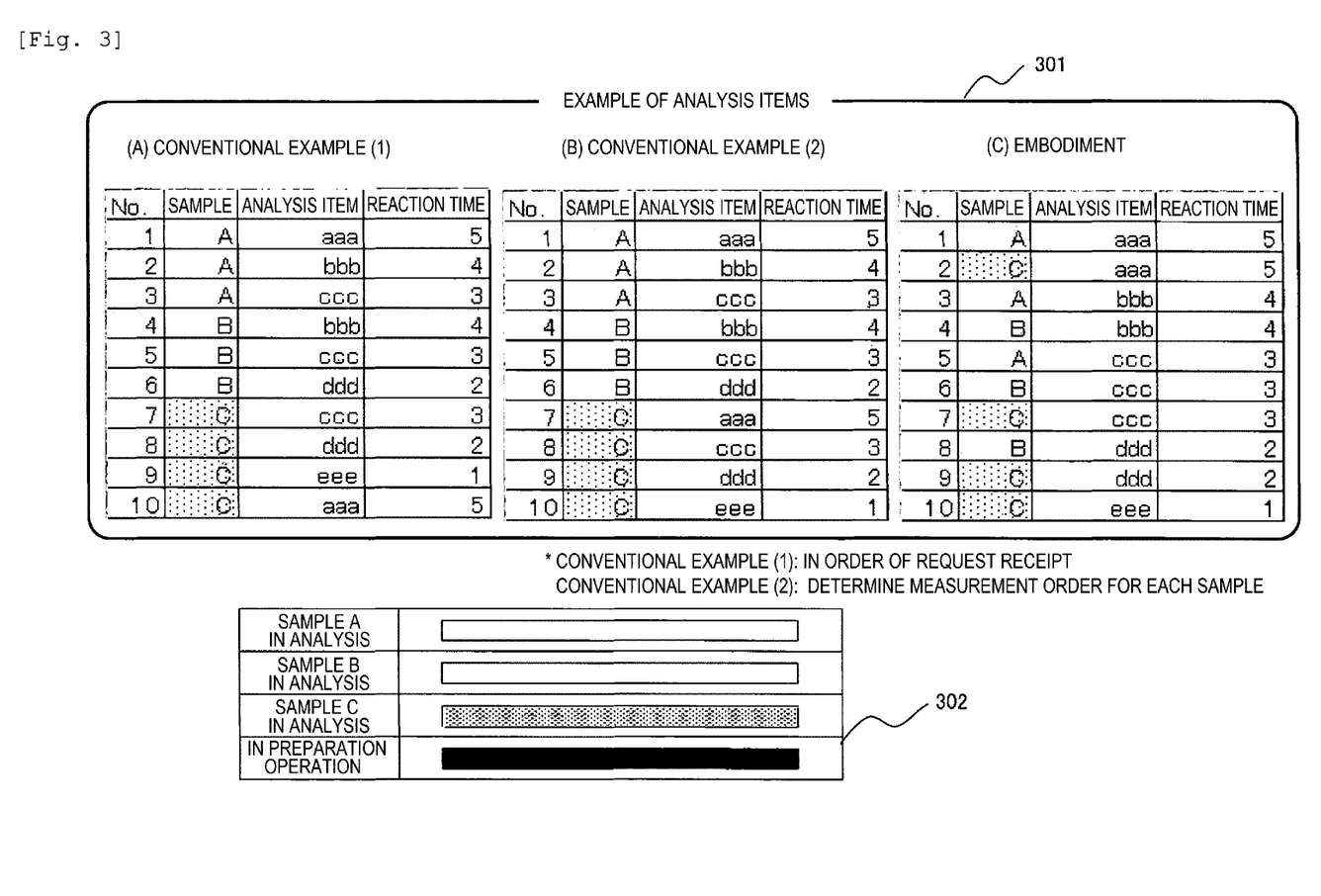
FIG. 3 is a schematic diagram for comparing relationships of measurement times between a measurement order in the case where the embodiment (the first embodiment) is applied and measurement orders determined by conventional techniques.

FIG. 3 is a schematic diagram for comparing relationships of measurement times between a measurement order in the case where the embodiment is applied and measurement orders determined by conventional techniques. FIG. 3 specifically shows an example where a blood clotting test with 10 items in total is performed according to an analysis item example shown in 301. 301(A) is a conventional example (1) and shows a measurement order in the case where measurements are performed in the order of request receipt. 301(B) is a conventional example (2) and shows a measurement order which is determined for each sample. 301(C) shows a measurement order which is determined beyond the difference in sample types according to the embodiment. 302 shows a criteria to indicate in-analytical operation of each sample and in-preparation for the operations. 303 is a timing chart in the measurement order determined by the conventional example (1) and shows the time until analyses are complete in the case of measurements in the order of request receipt. 304 is a timing chart in the measurement order determined by the conventional example (2) and shows the time until analyses are complete in the case of analyses in descending order of the reaction time length for each sample. On the other hand, 305 is a timing chart where the measurement order is determined according to the embodiment and shows the time until analyses are complete in the case where reaction times for all test items for a plurality of samples beyond the difference in sample types is taken into account. 303, 304 and 305 each represents usages of the 1st to 6th ports in the reaction ports 108.

As shown in FIG. 3, in comparison of 303, 304, and 305, the time until the analyses are complete for all test items for all samples requested beyond the difference in sample types can be shortened in the analyses by the measurement order according to the embodiment as compared with the analyses by the measurement orders determined by the techniques of the conventional example (1) and the conventional example (2).

Specifically, in comparison between the timing chart 304 with the measurement order determined by the technique of conventional example (2) and the timing chart 305 with the measurement order according to the embodiment under the condition of the analysis item example 301 shown in FIG. 3, 305 where the measurement order according to the embodiment is applied resulted in earlier completion of the analyses by about 60 seconds.

Second Embodiment

In this embodiment, an aspect of analysis where not only the analysis time for all test items for a plurality of samples requested, but also the analysis completion time for each sample can be shortened will be described with reference to FIG. 4 and FIG. 5.

Figure 4:
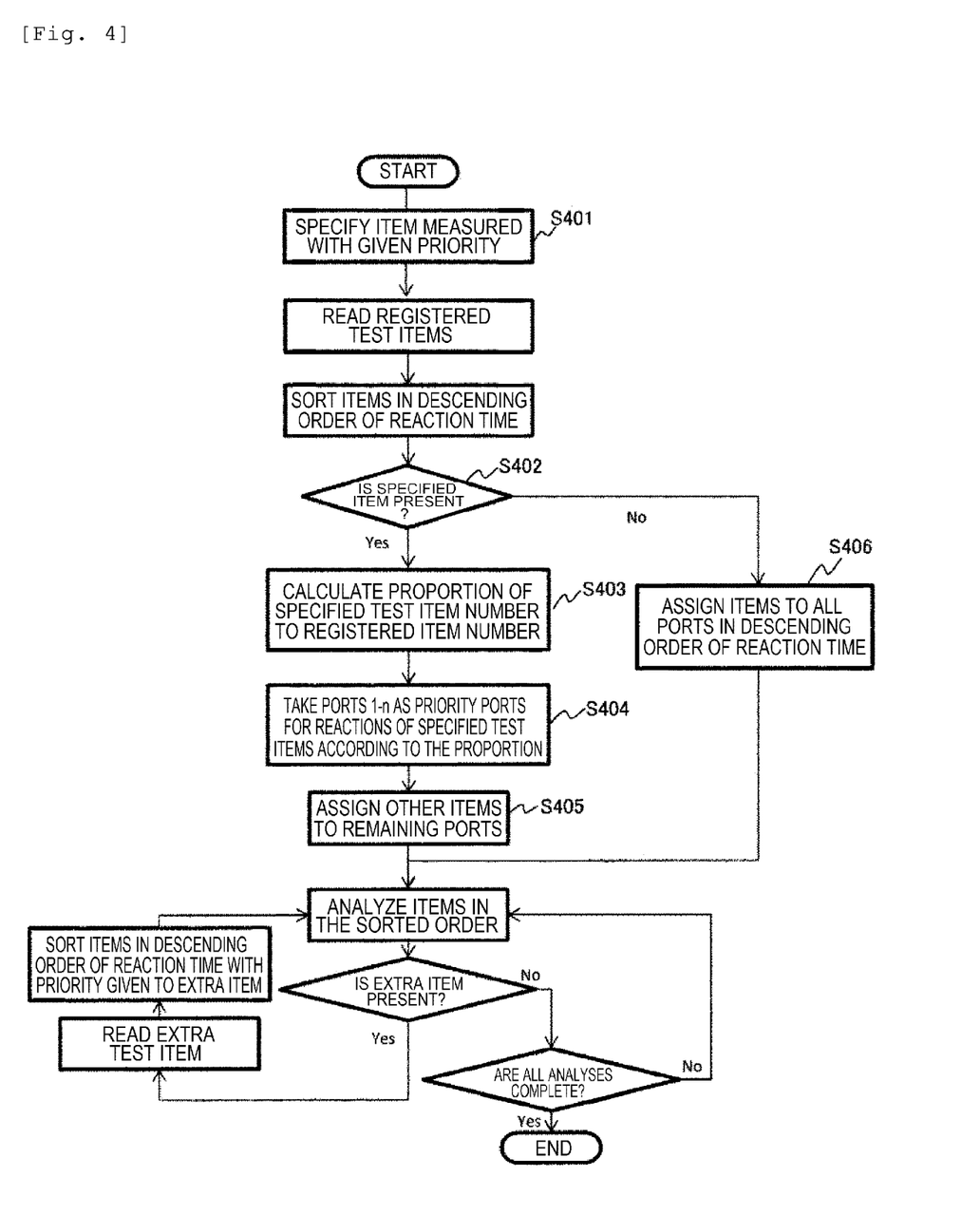
FIG. 4 is a flow chart for explaining an operation control for determining a measurement order of test items in the automatic analysis device according to the embodiment (a second embodiment).

FIG. 4 is a flow chart for explaining an operation control for determining the measurement order of test items in the automatic analysis device according to the embodiment (a second embodiment).

In the flow chart of FIG. 4, explanation of the part overlapping with the content described above in the flow chart of FIG. 2 is omitted.

In the embodiment, a configuration including a reaction port where a specified test item is preferentially analyzed will be described. Here, as an example, a mechanism for determining a priority port for a test item requiring a short measurement time will be described, but the embodiment is not limited to the example, and other conditions for specification can be adopted.

In FIG. 4, the item to be measured in the priority port is specified (step S401). This is performed by a user via the operating unit 115 shown in FIG. 1. A case where a test item requiring a measurement time of 1 minute is specified as the item to be measured in the priority port is described here, but what condition is adopted for the measurement in the priority port can be arbitrarily determined by a user.

Next, the measurement times of all items for all samples (which can be set here as 1 minute, 2 minutes, 3 minutes, 4 minutes, 5 minutes) are sorted in descending order, and then the presence or absence of any item for which a short measurement time (1 minute here) is set is checked (step S402). When an item or items requiring a measurement time of 1 minute are present, the proportion of the number of the items to the number of all the registered items is calculated (step S403). For example, if the 200 test items are registered in total and the number of the requested items that requires a measurement time of 1 minute is 30 for all the samples, the proportion is 30/200=0.15 (15%).

Reaction ports of the number corresponding to the thus obtained proportion are allocated as the reaction ports for preferentially analyzing the test items requiring a measurement time of 1 minute (step S404). For example, in a configuration of the automatic analysis device in which the number of the reaction ports is 6 as described in FIG. 1, when the proportion of the test items requiring 1 minute is 15%, the number of the reaction ports where the test items requiring a measurement time of 1 minute are preferentially measured is 6 ports×0.15=0.9 1 port, and the 6th port is used as a priority port for the test items requiring a measurement time of 1 minute.

In the priority port, test items for which the measurement time is set to 1 minute are preferentially analyzed as described above. When the test items requiring 1 minute become absent or when, for example, an analysis for a higher-priority item such as an urgent specimen is allocated, the 6th port as a priority port may be used for another analysis.

When step S402 determines that there is no test item requiring a measurement time of 1 minute, the reaction ports are allocated in descending order of the measurement time length (step S406) in the same manner as in FIG. 2.

The effect of the embodiment configured described above will be explained. In the first embodiment, all test items for all samples to be measured are re-sorted in descending order of the measurement time length and the analyses are performed. According to the aspect, the analysis completion times of all test items can be shortened but when focused on the measurement time for each sample, the time until the analyses for one sample are complete may not be necessarily shortened. For example, when test items requiring measurement times of 1 minute and 5 minutes are requested for one sample, the item requiring a measurement time of 5 minutes is analyzed in an earlier stage under the mechanism for determining the analysis order and the test item requiring a measurement time of 1 minute is analyzed later among all the analysis items. Accordingly, when acquirement of analysis results is required for each sample, it may take a long time from start of the analyses to the acquirement.

Particularly in a blood clotting analysis, three items of prothrombin time (PT), activated partial thromboplastin time (APTT), and fibrinogen (Fbg) are sometimes analyzed. It takes several minutes to complete a blood clotting reaction for PT, whereas it takes several tens of seconds to complete a blood clotting reaction for Fbg. The measurement times are also different depending on the test items. As described above, difference may be arise in the analysis timings due to the difference in measurement times for test items even in test items for the same sample. This results in a problem in that the timing of acquisition of the results for all test items requested for the same sample is delayed.

In contrast, in the embodiment, a priority port where items requiring a shorter measurement time are preferentially measured is provided. Furthermore, the embodiment includes a control mechanism in which the number of the priority ports is determined based on the proportion of the number of items requiring the shorter measurement time to the total number of test items. This leads to reduction of the time for acquisition of all the results of test items requiring different measurement times requested for the same sample, and thus the test results can be rapidly provided to a user. The embodiment illustrates an example where a priority port for items requiring a measurement time shorter than a prescribed time (1 minute) is provided. However, the embodiment covers examples where a priority port is provided for test items requiring a longer measurement time (for example, 4 minutes, 5 minutes, etc.), or for a specific test item under the same control mechanism.

Figure 5:
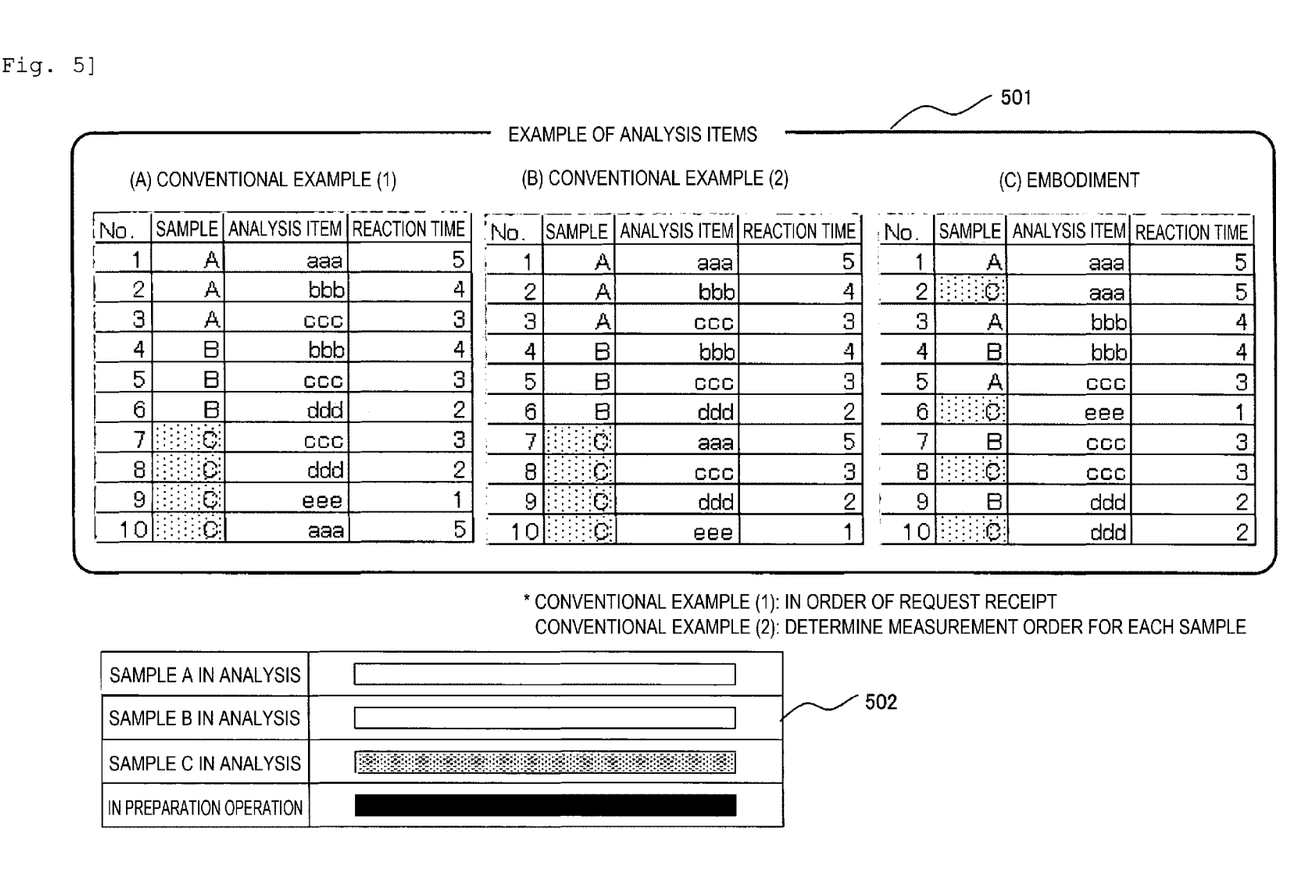
FIG. 5 is a schematic diagram for comparing relationships of measurement times between a measurement order in the case where the embodiment (the second embodiment) is applied and measurement orders determined by conventional techniques.

FIG. 5 is a schematic diagram for comparing relationships of measurement times between a measurement order in the case where the embodiment is applied and measurement orders determined by conventional techniques. The analysis item example 501 (501(A) to 501(C)) shown in FIG. 5 and a criteria 502 to indicate in-analytical operation of each sample and in-preparation for the operations are similar to 301 and 302 in FIG. 3. That is, 501(A) is a conventional example (1) and shows a measurement order in the case where measurements are performed in the order of request receipt. 501(B) is a conventional example (2) and shows a measurement order which is determined for each sample. 501(C) shows a measurement order which is determined beyond the difference in sample types according to the embodiment. 503 is a timing chart in the measurement order determined by the conventional example (1) and shows the time until analyses are complete in the case of the measurement in the order of request receipt. A measurement order 504 is a timing chart in the measurement order determined by the conventional example (2) and shows the time until analyses are complete in the case of analyses in descending order of the reaction time length for each sample. 505 is a timing chart in the case where the measurement order is determined according to the embodiment, and shows the time until analyses are complete in the case of using a priority port where items requiring a shorter measurement time are preferentially measured while taking into account the reaction times of all test items for a plurality of samples beyond the difference in sample types. 503, 504, and 505 each represents usages of the 1st to 6th ports in the reaction ports 108.

As shown in FIG. 5, in comparison of 503, 504, and 505, the time until the analyses are complete required for all test items for all samples requested can be shortened in the case of analyses by the measurement order according to the embodiment as compared with the case of analyses by the order of request receipt or by the measurement order determined by a conventional technique.

In comparison between 504 and 505 under the condition of analysis item example of 501 shown in FIG. 5, the case of adopting the measurement order according to the embodiment results in earlier completion of the analyses by about 60 seconds.

Thus, according to the embodiment described above, not only the analysis time for all test items for a plurality of samples requested, but also the analysis completion time for each sample can be shortened together.

REFERENCE SIGNS LIST

100 Automatic analysis device
101 Sample vessel
102 Sample disk

103 Reagent vessel
104 Reagent disk
105 Sample dispensing mechanism
106 Sample dispensing position
107 Reaction vessel
108 Reaction vessel placement unit
109 Reaction vessel transporting mechanism
110 Reaction vessel stock unit
111 Reaction port
112 Reagent dispensing mechanism
113 Reagent dispensing mechanism washing mechanism
114 Reaction vessel disposing unit
115 Operating unit
116 Control unit
117 Storage unit
118 Interface
301, 501 Analysis item example
302, 502 Criteria to indicate in-analytical operation of each sample and in-preparation for the operations

The invention claimed is:

1. An automatic analysis device comprising:
a sample vessel for holding a sample;
a reagent vessel for holding a reagent;
a plurality of reaction vessels;
a sample dispensing mechanism for dispensing the sample to one or more of the plurality of reaction vessels from the sample vessel;
a reagent dispensing mechanism for dispensing the reagent to the plurality of reaction vessels such that each one of the plurality of reaction vessels has formed therein a respective one of a plurality of mixed solutions;
an analysis unit that includes a plurality of reaction vessel placement units in a single reaction port for placement of the plurality of reaction vessels therein, each of the plurality of reaction vessel placement units being provided with a light source for emitting light to each of the plurality of reaction vessels placed therein and a light receiving unit for receiving the light emitted from the light source;
an operating unit for input of information about the sample; and
a control unit configured to control the analysis unit and allocating a first proportion of the plurality reaction vessel placement units to receive one or more of the plurality of reaction vessels based on:
comparing predicted reaction time lengths of the analysis items for each of the plurality of mixed solutions to a predetermined time condition, wherein said predetermined time condition is an upper or lower threshold length of time,
determining a second proportion of the plurality of mixed solutions having analysis items for which the predicted reaction time lengths satisfy the predetermined time condition in relation to the total number of the plurality of mixed solutions, and
allocating the first proportion of the plurality of reaction vessel placement units for placement of one or more of the plurality of reaction vessels having a mixed solution associated with a predicted reaction time length that satisfies the predetermined time condition based on the determined second proportion.

2. The automatic analysis device according to claim 1, wherein the predetermined time condition is satisfied when the predicted reaction time length is shorter than the predetermined time condition.

3. The automatic analysis device according to claim 1, wherein the predetermined time condition is satisfied when the predicted reaction time length is longer than the predetermined time condition.

4. The automatic analysis device according to claim 1, wherein the predetermined time condition is associated with a specific analysis item.

5. The automatic analysis device according to claim 1, wherein when a request of an analysis for an extra sample arises in the analyses, the control unit controls the analysis unit to preferentially analyze the extra sample regardless of the determined analysis order.

* * * * *